United States Patent [19]

Oliveira

[11] 4,099,886
[45] Jul. 11, 1978

[54] DETECTING SYSTEM

[75] Inventor: Robert J. Oliveira, Maplewood, Minn.

[73] Assignee: Minnesota Mining and Manufacturing Company, Saint Paul, Minn.

[21] Appl. No.: 704,175

[22] Filed: Jul. 12, 1976

Related U.S. Application Data

[62] Division of Ser. No. 601,384, Aug. 4, 1975, Pat. No. 3,992,096.

[51] Int. Cl.² ............................................. G01N 21/04
[52] U.S. Cl. .................................. 356/244; 23/253 TP
[58] Field of Search ....................................... 356/36–38, 356/102, 244; 350/92, 94; 23/253 TP

[56] References Cited

U.S. PATENT DOCUMENTS

| | | | |
|---|---|---|---|
| 3,666,421 | 5/1972 | Price | 23/253 TP |
| 3,672,845 | 6/1972 | Verbeck | 23/253 TP |
| 3,794,467 | 2/1974 | Adams et al. | 23/230 R |
| 3,963,441 | 6/1976 | Dietrich | 23/253 R |

Primary Examiner—John K. Corbin
Assistant Examiner—Matthew W. Koren
Attorney, Agent, or Firm—Cruzan Alexander; Donald M. Sell; Carolyn A. Bates

[57] ABSTRACT

A method is disclosed for detecting the formation of or presence of light-interacting domains, e.g. particles or clumps of particles, in a supporting medium which comprises: disposing the supporting medium between a source of multipoint ilumination and a scintillation detector, illuminating the supporting medium with a multiplicity of discrete light beams directed through the medium toward the scintillation detector; and causing relative motion between the light beams and the supporting medium. If light-interacting domains of critical size are present in the medium scintillation is detected. A viewer and test card for carrying out the method are also disclosed.

3 Claims, 5 Drawing Figures

DETECTING SYSTEM

This is a division of application Ser. No. 601,384 filed Aug. 4, 1975, now U.S. Pat. No. 3,992,096.

BACKGROUND OF THE INVENTION

This invention relates to a method for detecting the formation of or presence of light-interacting domains supported by a medium. A particular aspect of the invention relates to a method of detecting particles or clumps of particles in a supporting medium. A more particular aspect of the invention relates to a method for detecting the occurrence of agglutination between antigens and their corresponding antibodies in conventional immunological diagnostic test procedures. Also included within the scope of the invention is a viewer for practicing the method of the invention.

A number of pathological conditions, as well as certain nonpathological states such as pregnancy, are routinely diagnosed through the application of well known principles of immunology. When the human or animal body is exposed to a foreign protein (antigen) the body's natural defense mechanism is triggered to produce an antibody corresponding to the invading antigen. When an antigen and its corresponding antibody come into contact with each other under the proper conditions, agglutination or agglomeration occurs, and a complex is formed which is generally less soluble than either the antigen or the antibody. This antigen-antibody reaction is the basis of most immunological diagnostic tests. In most tests a reagent containing a known antigen or antibody is added to a test medium containing serum or other body fluid from the patient. If agglutination is observed, conclusions can be made concerning the presence or absence of the corresponding antigen or antibody in the test medium. In order to provide an efficient diagnostic procedure, the presence or absence of agglutination in the test medium must be readily discernable. This has been a problem with many antigen-antibody systems wherein agglutination proceeds slowly or the particle size of the agglomerate is too small to be observed with the naked eye. This problem has been alleviated to some degree by adding a carrier material such as polystyrene latex to the antigen or antibody to form the known reagent. In a test procedure the use of a latex-protein reagent results in the formation of agglomerates which are larger and easier to observe. However, even when a carrier material is present, the visual observation of agglutination in the test medium is often difficult. As a result, the accuracy of many immunological diagnostic procedures depends greatly on the individual skill and experience of the technician conducting the test.

A number of devices have been developed for the purpose of detecting the formation of or presence of particles in a supporting medium. Some of these devices have particular application in the area of immunological diagnostic testing. For example, U.S. Pat. No. 3,432,268 describes a method and device for testing a suspension of agglutinable cells. The device operates by passing a simple beam of light through a continuous stream of a cell suspension as it is mixed with the reagent. If agglutination occurs, the cells are taken out of suspension and the ability of the suspension to transmit light is increased. A photometric system of the spectrophotometric or nephelometric type is used to detect changes in light transmission.

Another method using photoelectric means to detect agglutination is described in U.S. Pat. No. 3,463,614. The test medium containing reagent and test fluid is contained in the capillary tube. To detect clumping, a thin beam of light is directed transversely through the reciprocating capillary tube, and if clumps are present, modulation of the light beam occurs which is detected by a photodiode. The output voltage from the photodiode is coupled with conventional electric circuitry to provide a qualitative measure of agglutination.

Other examples of agglutination detecting methods using light modulating and light scattering techniques are found in U.S. Pat. Nos. 3,520,609 and 3,819,271, respectively.

Each of the methods described above has certain shortcomings in that either sophisticated and costly optical and electronic instrumentation are required, or interpretation of the results is difficult and/or time consuming.

DESCRIPTION OF THE INVENTION

The system of the present invention overcomes many of the shortcomings associated with prior art systems and provides a convenient, efficient, easy-to-use and inexpensive means for detecting light-interacting domains in a supporting medium.

The term "light-interacting domains" as used herein refers to discrete areas or entities, supported by a medium, which possess different light-transmitting properties than the supporting medium. Generally, light-interacting domains are particles or clumps of particles. However, they may also be non-particular in nature such as interruptions or irregularities in a discontinuous monolayer or film, or they may be discrete droplets of a substance dispersed in a medium, such as may exist in an emulsion. The phrase "supported by a medium" means that the particular light-interacting domains may be contained in the medium, e.g. particles in a fluid or gel, or deposited on the surface of a substrate, e.g. as a film.

The system of the present invention utilizes a phenomenon which shall be referred to as "scintillation" to observe light-interacting domains supported by a medium. Scintillation is a sparkling or flickering effect produced as individual light beams in a multipoint light field appear to randomly flash on and off.

The present invention provides a method of detecting light-interacting domains in a preselected size range supported by a medium which comprises disposing the medium between a source of multipoint illumination and a scintillation-detecting means, illuminating the medium with a multiplicity of discrete light beams directed through the medium toward the scintillation-detecting means, and causing relative motion between the light beams and the medium. Alternatively, when the source of multipoint illumination and the medium are spaced from one another, the scintillation-detecting means may be caused to move relative to the light beams, the medium or both. When light-interacting domains are present in the supporting medium, the light beam will randomly flicker or scintillate as they interact with these domains.

This method provides a convenient means for observing tiny light-interacting domains which are otherwise invisible without the aid of magnification. The method is particularly suited for use in the medical diagnostic field for determining the presence of antigen-antibody interactions in conventional immunological tests. It is also well suited for detecting interactions between red blood cells in blood cross-matching tests, for identifying bacteria as well as other uses which will be disclosed hereinbelow. The method also has broad applicability outside the medical field in areas in which it is desirable to ascertain the presence of particles or inhomogeneities in a medium which are too small to be observed visually.

This method is especially suited for detecting light-interacting domains in the size range of about 0.5 to 250 microns, preferably 1 to 80 microns, at their broadest dimensions. Where particles or clumps of particles are to be detected, those smaller than about 0.5 microns will generally result in light scattering rather than scintillation, and those larger than 250 microns are readily observable without the necessity for optical enhancement. When non-particular light-interacting domains are detected, e.g., interruptions in a discontinuous monolayer, they will generally be in the same size range indicated above. As will be evident upon further disclosure of the invention, the method of the present invention may also be used to determine the apparent size as well as the presence of light-interacting domains in a particular supporting medium.

The critical elements of the system of the present invention are (1) a source of multipoint illumination; (2) means for disposing the supporting medium between the source of multipoint illumination and the scintillation detecting means, and (3) means for generating relative motion between the light beams and the supporting medium.

Sources of multipoint illumination useful in practicing the invention conveniently are transmitting or reflecting surfaces which will take light from a single source such as a light bulb and divide it into a multiplicity of discrete light beams. Thus, the discrete light beams may be produced by a suitable retroreflective surface illuminated from above or by an opaque surface containing tiny openings or transparent areas illuminated from below.

A particularly useful source of multipoint illumination is a retroreflective surface composed of a monolayer of glass beads immobilized in, for example, a black pigmented resin. This type of surface can be illuminated from above by a single light source and each glass bead will generate a beam of reflected light. The size of the glass beads and the index of refraction of the resin will determine the apparent diameters of the reflected light beams. Retroreflective surfaces of this type are commercially available under the trademark Scotchlite ® from the 3M Company.

Other retroreflective surfaces which may be used include liquid films containing retroreflective beads suspended therein. An example of such a surface is a film containing Codit ® retroreflective beads.

For purpose of the invention a wide variety of other types of surfaces can also be used for dividing direct light into a multiplicity of discrete light beams. Any surface having suitably small, discrete openings or transparent areas for transmitting light can be used. Particularly suitable are half-tone screens commonly used in the photographic art. Also useful are surfaces formed by a cross section of a bundle of fiber optics. Frosted glass, embossed and other surfaces which transmit light in discrete areas are also suitable. It is not necessary that the light beams generated by the source of multipoint illumination be uniform and regularly spaced.

The apparent diameters of the individual light beams illuminating the supporting medium depend upon the diameter of the light transmitting areas in the surface or, in the case of retroreflective surfaces, upon the diameter of the individual retroreflective portions, e.g., glass beads. The apparent diameters of the light beams can be readily measured by photomicrographic techniques. When selecting a surface for generating multipoint illumination in a particular test procedure, some consideration must be given to the size of the light-interacting domains which are to be detected.

To detect particular or non-particular light-interacting domains in the size range of about 0.5 to 250 microns by the scintillation method the supporting medium is preferably illuminated by multipoint illumination wherein the ratio of the apparent diameter of the individual light beams (as measured photomicrographically) to the apparent diameter of the domains is approximately 50/1 to 1/10. The exact ratio is not critical within broad limits and optimum conditions will vary from test to test depending upon such factors as the distance between the supporting medium and the multipoint illumination surface, the displacement velocity and the light transmitting properties of the domains. For most purposes, surfaces generating light beams between 10 and 100 microns in diameter will be used.

As indicated above, in order for scintillation to occur, there must be relative motion between the individual light beams and the supporting medium, or alternatively between the scintillation detecting means and the test medium or light beams when the latter are spaced from one another. This motion is most conveniently accomplished by moving the supporting medium transversely or up and down relative to a stationary multipoint surface. The displacement velocity may vary greatly depending upon the size of the light-interacting domains and the size of the light beams. In the case of very small particles, e.g., 0.8 microns, which are suspended in a fluid medium, no externally generated motion is required in order to produce scintillation. This is apparently due to the inherent random movement (Brownian motion) of the particles in the fluid. For larger domains, e.g., 5.0 microns and larger, the displacement velocity will generally range from 1 to 30 cm/min. In any event, the optimum displacement velocity is readily determined empirically by an observer manually moving the supporting medium in various directions relative to the light source.

The scintillation effect is ordinarily most easily observed visually. However, other means for detecting scintillation are available in the art and can be adapted for use in the system. Examples of such means include solid state scanning arrays, e.g., a charge coupling device, flying spot scanner or image detector, each being coupled with a memory device. Sequential photographs may also be used to gather scintillation information.

The supporting medium is preferably disposed as a thin layer or film between the multipoint illumination surface and the scintillation detecting means. This is of greatest importance when the supporting medium is a liquid containing particles to be detected, in which case a thin layer of the liquid will reduce the likelihood of particles masking one another from above or below. This masking effect tends to make the particles appear larger and may result in some distortion. Thus, a liquid supporting medium is generally disposed as a drop or several drops directly on the multipoint illumination surface or spaced from the surface on a transparent flat surface such as a plastic film or glass slide. The supporting medium may also be a dry film deposited on the surface of a transparent substrate by evaporation of a liquid containing particles or by the settling of particles from the air.

It is also desirable that the concentration of light-interacting domains supported by the medium be kept relatively low. A high concentration may result in too much interaction with the light beams thereby reducing the number of light beams which are flashing on and off at any given moment. The optimum concentration will vary somewhat depending upon the type of test being conducted, but generally the concentration of light interacting domains in the supporting medium should be less than 10 percent by volume when the medium is a liquid. When a dry film medium is used, the concentration of particles in the liquid prior to evaporation of the liquid is also preferably less than 10 percent by volume.

The present invention has broad utility in detecting the presence of light-interacting domains in a supporting medium. It is particularly useful in the medical area for detecting particle clumping reactions involving biological material. The term "biological materials" refers to any substance which is found in or part of a living organism. In particle clumping reactions a reagent is generally used which is known to react with specific biological material to be detected and cause clumping to occur. Biological materials conventionally detected in this fashion are cells, e.g. blood or microbial, and various types of antigens and antibodies. Typical particle clumping reactions include agglutination tests such as those used to detect pregnancy, rheumatoid factor, infectious mononucleosis, lumpus erythematosis, gonorrhea, bacterial infections, etc. These tests are generally of two types, direct and indirect. Agglutination indicates a positive reaction with a direct test and a negative reaction with an indirect test. Direct agglutination tests typically utilize a carrier particle, e.g. polystyrene latex, which is coated with a substance capable of interacting with the biological material being determined. Indirect agglutination tests utilize one reagent which is a carrier particle coated with the biological material being determined and a second reagent which is an agglutinating agent. Conventional agglutination tests are conducted in a fluid medium and the test sample is generally a body fluid such as blood, urine, etc. The unagglutinated latex reagent is normally made up of particles less than 1 micron in diameter and is milky in appearance. An agglutination reaction is generally indicated by macroscopically observable clumping in which submicron latex particles coalesce to particles hundreds of microns in diameter.

Using the method and viewer of the present invention, it is possible to detect the presence of agglutination before the clumped particles become large enough to be seen with the naked eye. Thus, an improvement in sensitivity results. Moreover, readability is significantly improved because all particle clumps, irrespective of their gross form or shape, result in one observable phenomenon, scintillation. This is unlike the conventional interpretation of macroscopically observed clumps, where description varies, e.g., clumps, flecks, granules, etc., with different test and observers. Another advantage of using scintillation to visualize particle clumping reactions is that one views the sample in its entirety with a resolution as low as a few microns. Since the unaided normal eye can resolve particles only as small as approximately 50 microns in diameter, one must resort to magnification to get similar resolution by traditional techniques. In doing so, field of vision is restricted in a direct relationship to magnification.

The system of the present invention also provides a convenient method for examining interacting particles in the dry state. Blood cross-matching tests, febrile antigen tests, bacterial identification, etc. are preferably carried out in this manner. For these tests it is desirable to place a test solution or suspension of a predetermined concentration of particles, e.g. cells, on a clear surface and allow or cause the liquid to evaporate. The concentration and surface area are chosen so that when there is no interaction between the particles an essentially continuous monolayer or film will be deposited on the surface. The continuous monolayer will transmit light uniformly and no scintillation will be observed when the film is examined by the present method. If there is even a slight interaction between the particles a discontinuous monolayer will be deposited with interruptions occuring as a result of particle/particle interaction. When illuminated by multipoint illumination these interruptions will cause scintillation to occur.

It will also be obvious to one skilled in the art that certain reactions wherein the particles are decreased in size (such as in cell lysis) can be observed with the present system. In a liquid medium, particle disruption results in the disappearance of scintillation as particle size decreases below that critical for scintillation. In the dry state, careful selection of concentration of suspensions to be dried on a predetermined surface area can produce films which will scintillate in the absence of particle disruption prior to dry-down, and which will not scintillate if particle disruption occurs prior to complete dry-down.

It is also possible to determine the size of various light-interacting domains with the scintillation method. This is accomplished by selecting a multipoint illumination surface which generates light beams of a known size whereby only light-interacting domains above a known critical size will cause scintillation. When this procedure is followed, it is also important to carefully control displacement velocity. The relationship between light beam size, particle size and displacement velocity is illustrated in example 5 below.

In areas outside of the medical area, the present invention can be used to detect the presence of contaminants of a critical size in a gaseous or liquid medium. It can be used to determine the end point of a phase titration, the presence of fine precipitates in various analytical tests, as well as many other applications where knowledge of the presence of light-interacting domains in a medium is desired.

DESCRIPTION OF THE DRAWINGS

Understanding of the invention will be facilitated by reference to the accompanying drawings wherein.

Figure 1:
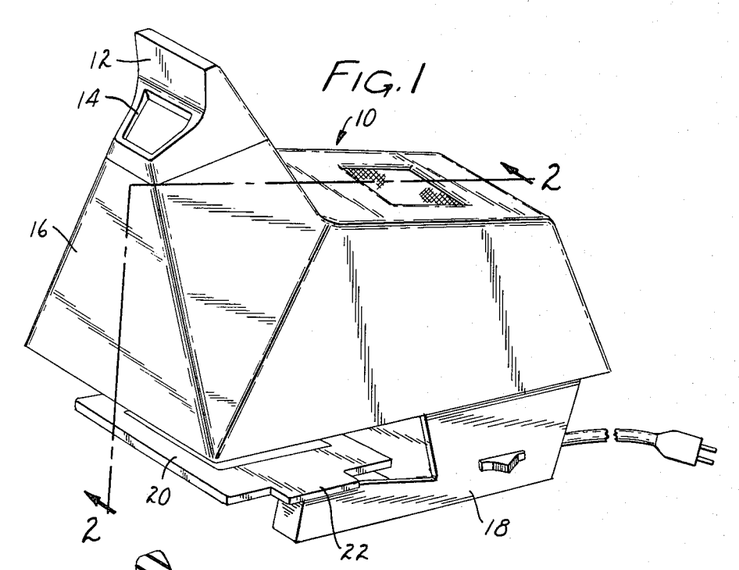
FIG. 1 is a prospective view showing the front, top and one side of the viewer constructed in accordance with the present invention.

In FIG. 1 the exterior of viewer 10 is shown containing eyepiece 12 having a window 14 through which a human observer looks to observe scintillation. Housing 16 surrounds the observer's field of vision and prevents glare from room lighting. The lower portion of housing 16 is attached to and supported by frame 18. Viewing stage 20 is attached to frame 18 and is positioned so that its upper surface is viewable through eyepiece 14. Viewing stage 20 supports the sample of test medium during the test procedure. Viewing stage 20 is preferably black or a dark color to reduce glare from light impinging upon it and is pivotally supported by frame 18 and movable through a vertical arc. Finger press 22, extending from viewing stage 20 and continuous therewith allows the human operator to manually control the movement of viewing stage 20. In this embodiment a retroreflective surface such as a sheeting containing immobilized glass beads is placed upon viewing stage 20. The test medium to be analyzed is deposited directly on the retroreflective surface or alternatively on a thin optical plate or film which is placed over the retroreflective surface.

Figure 2:
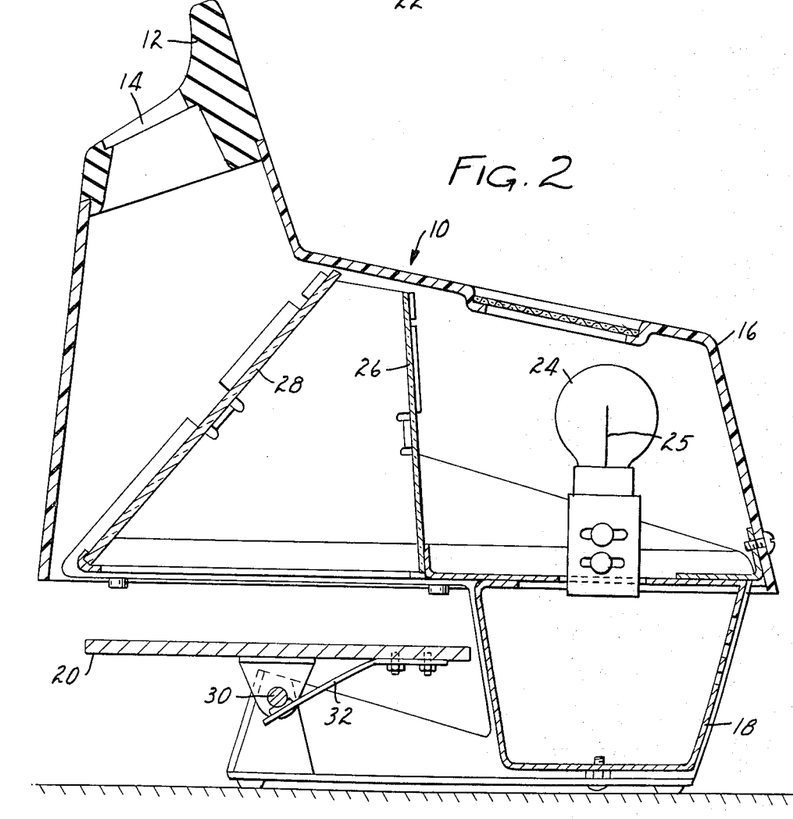
FIG. 2 is a cross-sectional view taken along line 2—2 of FIG. 1.

FIG. 2 is a cross-sectional view of viewer 10 wherein housing 16 supports and encloses lamp 24, condensing lens 26 and beam splitter 28. Lamp 24 is supported centrally at the rear of housing 16 and it has a filament 25 which forms the source of light in the viewer. Lamp 24 is mounted on the top of the frame to place the longest dimension of the filament 25 parallel to the length of viewing stage 20. Lamp 24 may produce light of any visible wave length or multiplicity of wave lengths. The preferred embodiment of lamp 24 is a forty watt incandescent light bulb.

The condensing lens 26 is spaced forward of the lamp 24 with its axis horizontal and passing through the center of filament 25 of the lamp 24 to collect and transmit light from lamp 24 in parallel rays. The illustrated condensing lens is a Fresnel lens.

The beam splitter 28 is supported by the housing 16 in the path of the parallel rays of light transmitted by condensing lens 26 and at an angle to the optical axis of the lens and lamp to reflect a portion of the light from the condensing lens onto the viewing stage 20. When a retroreflective surface is placed on viewing stage 20, a portion of the light reflected from the beam splitter 28 is retroreflected from the surface directly back through the beam splitter 28 and through window 14 to be viewed by the observer. In the illustrated embodiment beam splitter 28 is a half-silvered mirror which is silvered on the side facing the condensing lens 26.

Viewing stage 20 is constructed so as to be movable by the operator. In the illustrated embodiment viewing stage 20 is attached to and supported by pivot shaft 30 which allows viewing stage 20 to be moved vertically through an arc of approximately 25°. A spring member 32 is attached to viewing stage 20 and friction fits against pivot shaft 30 to regulate the movement of the viewing stage.

Figure 3:
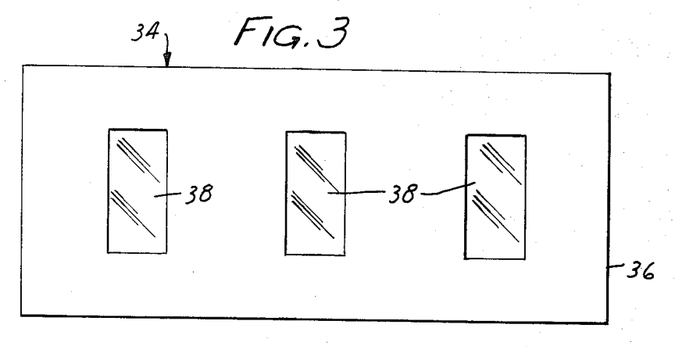
FIG. 3 is a plan view of a test card having a surface for generating multipoint illumination to be used with the viewer.

FIG. 3 is a plan view of the upper surface of a test card to be used with the viewer of the invention for carrying out conventional immunological tests. Test card 34 comprises a flat substantially rectangular substrate 36 having at least one circumscribed test area 38 on the surface thereof containing a dried deposit of a conventional immunological test reagent. The portion of the substrate 36 within the test area 38 must be capable of generating multipoint illumination when placed on the viewing stage and illuminated by a light source.

Preferably the substrate has a retroreflective surface containing immobilized glass beads which will generate multipoint illumination when illuminated from above. Alternatively, the substrate may be made up of a material having tiny holes or transparent areas such as a half tone screen which will generate multipoint illumination when illuminated from below. The dried immunological test reagent may be dried directly on the surface of the substrate or on a transparent film or plate placed over the substrate and adhered thereto. The immunological reagents which may be placed on the test card, their method of preparation, and the method of reconstituting them and mixing them with body fluids are known and described, for example, in U.S. Pat. Nos. 3,666,421 and 3,770,383.

When the immunological test reagents are reconstituted and mixed with the appropriate body fluid, the test card is placed on the viewing stage and the stage is moved slowly by the operator. If scintillation is observed, it can be concluded that agglutination or particle clumping has occurred producing light-interacting domains of critical size. Multiple test areas may be present on the test card. It is often helpful to have three test areas so that the unknown sample can be compared simultaneously with a positive control and a negative control.

Figure 4:
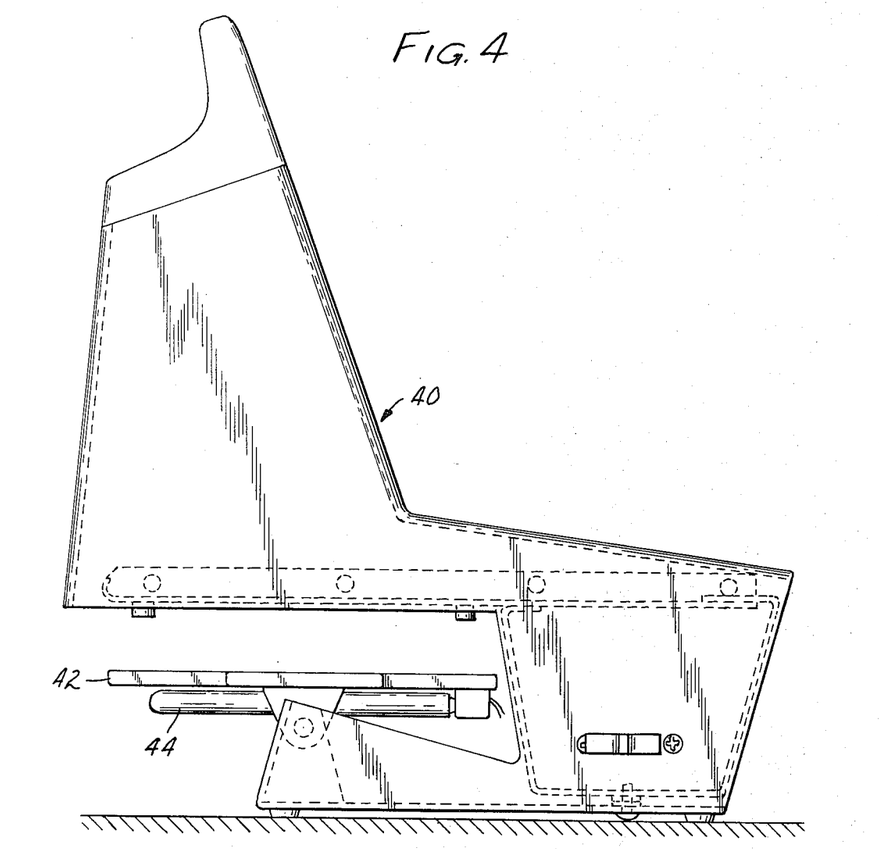
FIG. 4 is a cross-sectional view of an alternative embodiment of the viewer of the invention.

FIG. 4 shows an alternative embodiment of the viewer of the invention wherein viewer 40 contains viewing stage 42 which is capable of generating multipoint illumination itself when illuminated from below by lamp 44. Alternatively, viewing stage 42 may be transparent and a surface capable of generating multipoint illumination when illuminated from below is placed thereon. In the illustrated embodiment, lamp 44 is a fluorescent light bulb. In operation a liquid sample to be analyzed may be deposited directly on the multipoint illumination surface or on an optical plate which is placed over surface. When a dry sample is analyzed it is generally placed on an optical plate over the multipoint illumination surface. Relative motion may be generated between the individual light beams and the particles in the sample by moving the optical plate across the surface.

Figure 5:
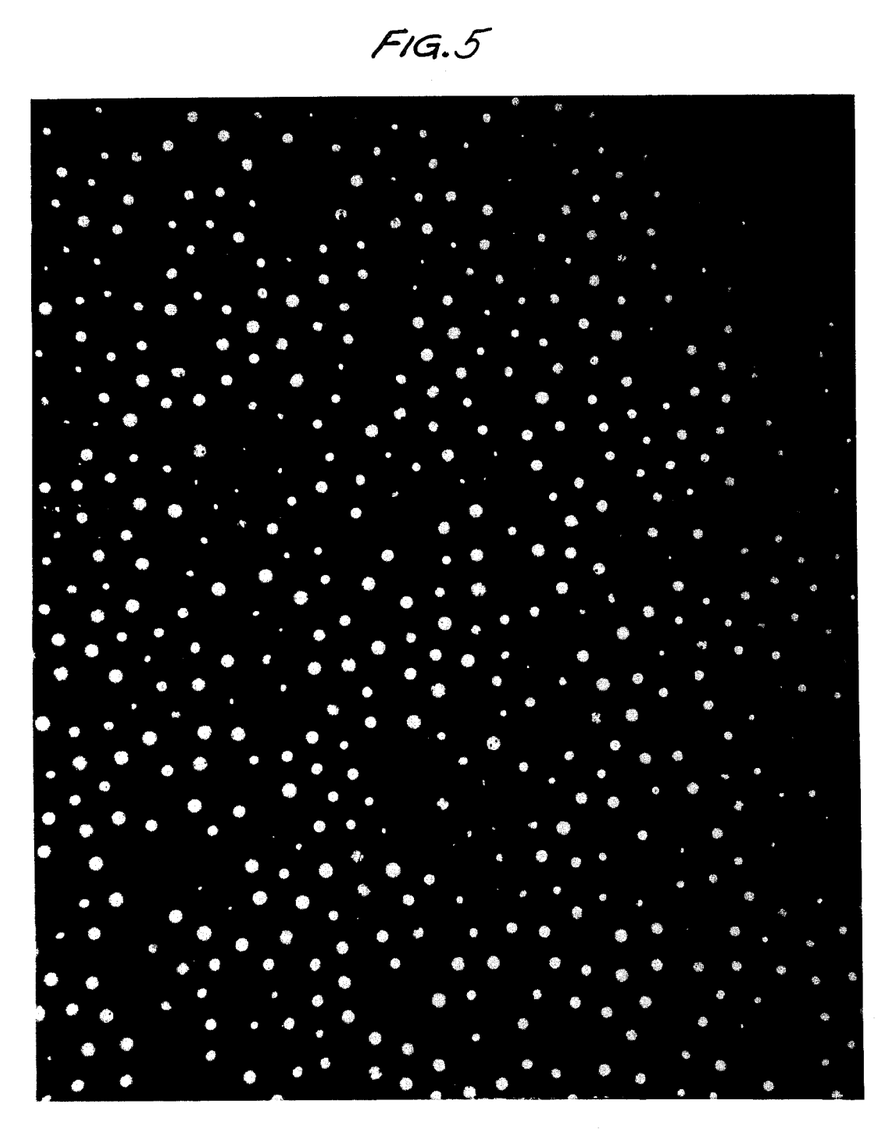
FIG. 5 is a photomicrograph of a retroreflective multipoint illumination surface.

FIG. 5 is a photomicrograph of a retroreflective surface containing immobilized glass beads which is consequently illuminated from above with a forty-watt incandescent light bulb. The individual light sources typically are 15 to 80 microns in diameter. When visual observation is employed, some consideration must be given to the size of the light source to avoid eye-stress.

Although the drawings depict the preferred embodiments of the invention, it will be obvious that the viewer can be constructed in many forms, and there is no requirement that elements of the apparatus be contained in a housing. If the room is sufficiently dark when the test procedure is carried out, one can observe scintillation without a housing if all the essential elements are present. When a retroreflective surface is used to generate multipoint illumination, a handheld viewer containing a light source and appropriate lens arrangement can be used. A suitable hand viewer such as that described in U.S. Pat. No. 3,832,038 can be used in connection with a retroreflective surface to observe scintillation.

Further understanding of the invention will be facilitated by the following nonlimiting examples:

EXAMPLE 1

Direct Latex Agglutination Pregnancy Test

A conventional latex reagent made up of particles approximately 0.8 microns in diameter coated with antihuman chorionic gonadotropin (anti-HCG) was obtained from a Wampole DAP ® pregnancy test kit. Two samples of human urine were used. The first sample (sample A) was taken from a nonpregnant individual and did not contain measurable amounts of human chorionic gonadotropin (HCG) activity. The second sample (sample B) was obtained from a pregnant woman and contained an HCG titer of 25.6 International Units per milliliter (Iu/ml).

One part of sample B was mixed with three parts of sample A, and serial dilutions were made producing urine samples differing in concentration of HCG by a factor of four.

Twenty-five microliters of the Anti-HCG latex (ultrasonicated for approximately 10 minutes) and a twenty-five microliter aliquot from each urine sample were mixed. The mixtures were rotated at 120 rpm's for 2 to 12 minutes. The mixtures were monitored for agglutination by Wampole's standard DAP ® procedure which consists essentially of placing a drop of the reagent-urine mixture on the surface of a test slide and rocking the slide gently for one minute. The appearance of the mixture is compared with the appearance of a latex control drop. If agglutination is noted in the test mixture, but not in the control, the test is deemed positive.

The mixtures were also monitored for agglutination by the scintillation method of the present invention. A few drops of each sample were placed on a Scotchlite ® retroreflective surface (containing glass beads of 15–80 microns in diameter). The surface was illuminated with a forty watt bulb in a viewer similar to that shown in FIG. 1. The fluid on the Scotchlite ® surface was moved in a vertical arc at a speed of approximately 16 cm/min. to generate movement of the particles in the sample. Results of the tests are shown in the following table.

| SAMPLE (HCG concentration) Iu/ml | CONVENTIONAL METHOD | SCINTILLATION METHOD |
|---|---|---|
| 25.6 (Sample B) | Positive (precipitate after 2 minutes) | Positive (Strong scintillation after 2 min.) |
| 6.4 | Positive (precipitate after 2 minutes) | Positive (Strong scintillation after 2 min.) |
| 1.6 | Questionable (very weak reaction, some precipitate after 3 min.) | Positive (Strong scintillation after 2 min.) |
| 0.4 | Negative (No reaction after 12 min.) | Negative (No scintillation after 12 min.) |
| 0.1 | Negative (No reaction after 12 min.) | Negative (No scintillation after 12 min.) |
| 0.0 (Sample A) | Negative (No reaction after 12 min.) | Negative (No scintillation after 12 min.) |

The above results indicate that the scintillation method improves the ability to discern a positive reaction from an apparent negative reaction, and that the present system provides an improvement over conventional procedures.

EXAMPLE 2

Latex Agglutination Test for Rheumatoid Factor

Samples of human sera of known decreasing amounts of rheumatoid factor titer were analyzed using the $R_3$ Screen Test ® from Wampole Laboratories, Stamford, Conn. Using the conventional procedure for the $R_3$ Screen Test ® a sample was selected which gave results indistinguishable from the negative control. This procedure consisted of mixing the serum, buffer solution and reagent together in a test tube, allowing the test tubes to stand overnight and viewing the test tubes against a dark background using indirect lighting. In a positive reaction tube, the agglutinated latex completely settles to the bottom of the tube or appears as macroscopically visible coarse clumps in suspension. A negative reaction tube is one in which no agglutination takes place and the suspension remains uniformly milky. The sample selected had a titer of 1/80.

This sample was then tested using the scintillation method of the present invention. The $R_3$ Screen Test ® reagents were used (except for the substitution of Hylands Glycine-Saline Reagent). The procedure which was followed consisted of mixing one drop of serum and one drop of buffer on a Scotchlite ® surface (containing immobilized glass beads 15–80 microns in diameter) adding two drops of latex reagent and rotating the resulting puddle for 3 minutes.

The surface was illuminated with a hand-held retroreflective viewer (Sight-O-Light, Wisconsin Electronics Corp., Racine, Wisconsin) while tipping the surface so that a liquid shear occurred within the puddle and movement of the particles was generated.

Three individuals were asked to read the results of the agglutination reactions conducted on a number of pairs of samples, (one negative for rheumatoid factor and the other weakly positive having a titer of 1/80) by the conventional procedure and with the scintillation method. The same reagents and mixing procedure was followed in all cases, and the samples were randomized. Each sample was scored and given a value between zero and four with four indicating the highest degree of agglutination. The results obtained with each method were compared.

Comparisons between the negative and weakly positive samples for each test method were made by paired "$t$" test. The results indicated that weakly positive samples analyzed by the scintillation method had a significantly higher average score than the negative samples, whereas weakly positive samples analyzed by the conventional method actually had a lower average score than the negative samples. These results illustrated the improved sensitivity of the system of the present invention.

EXAMPLE 3

This example demonstrates the selection of the optimum concentration of a suspension of essentially non-interacting red blood cells to be coated and dried per unit surface area on a clear film in order to form an essentially continuous monolayer. An essentially continuous monolayer uniformly transmits illumination and thus results in no scintillation.

A 25% by weight suspension of type "O" red blood cells was prepared in phosphate buffered saline from cells that had been washed three times in phosphate buffered saline. Dilutions of this solution with phosphate buffered saline were prepared which, when applied as uniformly deposited coatings on clear film, gave the approximate concentration of cells/cm² shown in the table below.

Each dried film was tested for scintillation using half-tone screens of varying sizes illuminated from below by twin 15-watt fluorescent light bulbs as the source of multipoint illumination. The results are shown in the following table wherein the degree of scintillation is expressed as a rating from 0 to +3. A zero rating indicates no scintillation. A +1/3 rating indicates almost no scintillation, while ratings of +1 and +2 indicate weak and moderate scintillation, respectively.

| Size Of Multipoint Illumination (Microns) | Relative Amount Of Scintillation Approximate Concentration of Red Blood Cells/Units Surface Area | | | | |
|---|---|---|---|---|---|
| | 3.9 mg/cm² | 3.8 mg/cm² | 1.45 mg/cm² | 1.02 mg/cm² | 0.37 mg/cm² | 0.14 mg/cm² |
| 14 | +⅓ | +⅓ | +⅓ | +1 | +2 | +2 |
| 25 | +⅓ | +⅓ | +⅓ | +1 | +2 | +2 |
| 49 | +⅓ | +⅓ | 0 | +1 | +2 | +2 |
| 80 | +⅓ | +⅓ | 0 | +1 | +1 | +1 |

Information from this example, i.e., the concentration of a suspension of essentially noninteracting cells that will result in a continuous monolayer of cells, is useful in selecting conditions for detecting slight interaction between cells. A concentration of a suspension of noninteracting red blood cells and a surface area on a clear film were chosen to result in the optimum conditions to give a continuous monolayer when dried on a clear film. The blood cross-match was conducted under these conditions in Example 4 below.

Information from this example is also useful in conducting tests to detect particle disruption such as cell lysis. The optimum concentration of cells and a surface area for deposition and subsequent drying which will result in a slightly non-continuous monolayer of cells is determined. A non-continuous monolayer will cause scintillation when viewed according to the method of the invention. Using this concentration of cells per unit surface area of deposition, one may determine whether cell lysis has occurred. Lysed cells will not occupy the same non-continuous monolayer as whole cells and thus lysed cells will not cause scintillation. Example 5 describes a cell lysis experiment.

EXAMPLE 4

Blood Cross-Matching Test

The following mixtures were prepared and analyzed using the scintillation method: (1) one drop of a saline suspension of type $A_1$ red blood cells and two drops of antisera to types A and B red blood cells; (2) one drop of a saline suspension of type $A_2$ red blood cells and two drops of a 1/80 dilution of antisera to types A and B red blood cells; and (3) one drop of a saline suspension of type 0 red blood cells and two drops of antisera to types A and B red blood cells. The saline suspensions each contained approximately 5 percent by weight of red blood cells which had been washed three times. (The antisera was obtained from Ortho Diagnostics, Ortho Pharmaceutical Corp.)

Each mixture was applied as a thin layer to a transparent plastic film which was placed over a half-tone screen containing 50 micron "holes" that were uniformly spaced 200 microns apart (measured from the center of one hole to the center of an adjacent hole). The half-tone screen was illuminated from below by twin 15-watt fluorescent light bulbs. The plastic film was moved slowly (approximately 10 to 20 cm/min) relative to the half-tone screen.

Mixture 1 showed immediate scintillation with a gradual disappearance of scintillation as particle clumps grew larger. Mixture 2 showed slight scintillation in the wet state, but showed dramatic scintillation when viewed after evaporation of the water.

Mixture 3 showed essentially no scintillation in either the wet or dry state. Neither mixtures 2 nor 3 showed any sign of clumping when viewed by normal non-microscopic means.

EXAMPLE 5

Cell Lysis Test

Two test solutions were prepared to determine whether the scintillation method could be used to distinguish lysed from unlysed cells. Solution No. 1 contained 1.5 ml of Streptolysin 0 buffer (from Lederle Laboratories) and 0.5 ml of type 0 red blood cells in 5% concentration. Solution No. 2 contained 1.0 ml of Streptolysin 0 buffer (from Lederle Laboratories), 0.5 ml of Streptolysin 0 (from Lederle Laboratories), a cell-lysing enzyme, and 0.5 ml of type 0 red blood cells in a 5% concentration.

Clear plastic films containing either drops of solution 1 or solution 2 which had been air dried were placed over a series of half-tone screens having hole diameters of 14, 25, 49 and 80 microns respectively. The screens were illuminated from below by twin 15-watt fluorescent light bulbs, and the clear films were moved at a speed of about 10–20 cm/min. The presence or absence of scintillation was determined in each case. The results are summarized in the following table.

| Hole Size (Microns) | Solution 1 (Control) | Solution 2 (Containing Lysing Enzyme) |
|---|---|---|
| 14 | Strong scintillation | Slight scintillation |
| 25 | Strong scintillation | Very slight scintillation |
| 49 | Slight scintillation around periphery | No scintillation |
| 80 | Very slight scintillation around periphery | No scintillation |

The half-tone screen containing 25 micron holes appears to be most useful in distinguishing lysed from unlysed red blood cells under the conditions of this test.

EXAMPLE 6

This example illustrates the relationship which should exist between particle size, size of the individual light beams, and displacement velocity in order to optimize scintillation.

Polystyrene particles obtained from Duke Laboratories having diameters of 5.0 and 20.0 microns and particles of 0.8 micron diameter obtained from Polyscience, Inc. were used as standards. These particles were tested as aqueous suspensions with each of a series of half-tone screens having hole diameters ranging from 14 to 80 microns illuminated from below.

For each particle size and each half-tone screen hole size, the velocity at which scintillation appeared and the velocity at which scintillation disappeared were determined. The results are summarized in the following table. The first velocity appearing in each group of two is the velocity at which scintillation appeared; the second velocity is that at which scintillation disappeared.

| Hole Size of Half-Tone Screen (Microns) | Velocities At Which Scintillation Appeared/Disappeared for Each Size Particle (cm/min) Particle Size | | |
|---|---|---|---|
| | 0.8 microns (0.025 wt% of solution) | 5.0 microns (0.029 wt% of solution) | 20 microns (0.05 wt% of solution) |
| 14 | 0/3.8 | 1.2/8.6 | 1.3/13.1 |
| 25 | 0/5.4 | 1.3/13.0 | |
| 32 | 0/14.2 | 1.8/16.7 | 2.1/18.4 |
| 50 | No scintillation | | |
| 80 | No scintillation | 4.8/21 | 3.8/20.0 |

This data indicates that higher velocities are required to both initiate and stop scintillation as particle size is increased. However, if the concentration of particles is increased to a point where the particles are behaving as groups, then nonparticle space can dominate the effect and one might want to slow down velocity to have scintillation occur. For any given particle size, higher velocities are needed to observe scintillation as the hole size of the half-tone screen (size of individual light beams) is increased. For particles as small as 0.8 microns, no externally generated velocity is needed to produce scintillation. No scintillation is observed when very small particles (0.8 microns) are illuminated with relatively large light beams (50 to 80 microns). These data also indicate that scintillation may vary in quality or amount and is not strictly an "all or nothing" phenomenon.

The particles used in this experiment were not opaque but rather semi-transparent polystyrene particles similar to those used in conventional immunological tests. The results may vary somewhat if opaque particles are used.

EXAMPLE 7

This example illustrates the use of scintillation to detect and demonstrate the presence of particles in air.

Fifty micrograms of Cabosil ® (fumed silica, Grade M-5, Cabot Corp., Boston, Mass.) were dispersed and suspended in a 27-liter bag. A 20 × 30 cm piece of polyester film (4 mil graphic arts base coated photographic film, 3M Co., St. Paul, Minn.) was covered on one side and half covered on the other side with removable pieces of protective film. This polyester film was suspended in the bag containing the Cabosil ® fumed silica particles for 1.5 minutes. After this exposure, the protective films were removed and the polyester film examined for scintillation on both the exposed and protected areas. Half-tone screens of varying sizes illuminated from below by twin 15-watt fluorescent light bulbs were used as the source of multipoint illumination. The results are shown in the following table wherein the degree of scintillation is expressed by a rating of 0 to +3. A rating of zero indicates no scintillation, while ratings of +1, +2 and +3 indicate weak, moderate and intense scintillation, respectively.

| Size Of Multipoint Illumination (Microns) | Degree Of Scintillation | |
|---|---|---|
| | Exposed Films | Unexposed Films |
| 14 | +1 | 0 |
| 25 | +1 | 0 |
| 49 | +2 | 0 |
| 80 | +2 − +3 | 0 |

Scintillation was best observed when the film was about 0.5 cm from the multipoint light source and the observer was about 40–45 cm from the multipoint light source.

EXAMPLE 8

This example illustrates the use of scintillation to determine the endpoint of a phase titration.

A series of volume/volume mixtures of carbon tetrachloride/isopropanol was prepared and ten milliliter aliquots were titrated with water to turbidity endpoint in the conventional procedure described by Rogers and Ozsogomonyan(Talanta, 1963, Vol. 10, pp. 633–639). Ten milliliter aliquots were also titrated with the method of the present invention using the onset of scintillation as the endpoint. Multipoint illumination was generated by means of an 80 micron diameter "hole" half-tone screen (200 micron distance from "hole" center to "hole" center) illuminated from below by a light box containing twin 15-watt fluorescent tubes.

| CONVENTIONAL ASSAY | |
|---|---|
| Carbon tetrachloride Isopropanol | Mls. of Titrant (H$_2$O) to Turbidity (Endpoint) |
| 80/20 | 0.30 |
| 70/30 | 0.40 |
| 60/40 | 0.80 |
| 50/50 | 0.82 |
| 40/60 | 1.59 |
| 30/70 | 2.60 |
| 20/80 | 5.17 |
| 10/90 | 9.77 |

| SCINTILLATION ASSAY | |
|---|---|
| Carbon tetrachloride Isopropanol | Mls. of Titrant (H$_2$O) to Scintillation (Endpoint) |
| 80/20 | 0.15 |
| 70/30 | 0.27 |
| 60/40 | 0.42 |
| 50/50 | 0.55 |
| 40/60 | 1.18 |
| 30/70 | 2.46 |
| 20/80 | 5.25 |
| 10/90 | 9.75 |

This example demonstrates a further utility of scintillation in that it permits an earlier and more uniform reading of phase titration endpoints than obtained by conventional methods.

What is claimed is:

1. A test card for preforming immunological tests on the surface thereof comprising a flat substrate which generates a multiplicity of discreet light beams of predetermined size when illuminated by a single light source having deposited thereon at least one dried immunological test reagent.

2. A test card for performing immunological tests on the surface thereof comprising a flat substrate having a plurality of retroreflective immobilized glass beads on the upper surface thereof and at least one dried immunological test reagent deposited on said upper surface.

3. A test card for performing immunological tests on the surface thereof comprising a flat substrate comprising a half tone screen and at least one immunological test reagent deposited thereon.

* * * * *